United States Patent
Sweeney et al.

(10) Patent No.: US 10,667,850 B2
(45) Date of Patent: Jun. 2, 2020

(54) MODULAR FEMORAL NAIL AND METHOD OF USE THEREOF

(71) Applicant: Spinal Generations, LLC, Mokena, IL (US)

(72) Inventors: Patrick J. Sweeney, Flossmoor, IL (US); Matthew V. Leyden, St. Paul, MN (US)

(73) Assignee: Spinal Generations, LLC, Mokena, IL (US)

( * ) Notice: Subject to any disclaimer, the term of this patent is extended or adjusted under 35 U.S.C. 154(b) by 53 days.

(21) Appl. No.: 15/679,773

(22) Filed: Aug. 17, 2017

(65) Prior Publication Data

US 2019/0053836 A1 Feb. 21, 2019

(51) Int. Cl.
*A61B 17/64* (2006.01)
*A61B 17/70* (2006.01)
*A61B 17/72* (2006.01)
*A61F 2/30* (2006.01)
*A61F 2/28* (2006.01)

(52) U.S. Cl.
CPC ........ *A61B 17/725* (2013.01); *A61B 17/6425* (2013.01); *A61B 17/7013* (2013.01); *A61B 17/72* (2013.01); *A61F 2002/285* (2013.01); *A61F 2002/2821* (2013.01); *A61F 2002/2825* (2013.01); *A61F 2002/30367* (2013.01); *A61F 2002/30405* (2013.01); *A61F 2002/30433* (2013.01); *A61F 2002/30495* (2013.01); *A61F 2002/30973* (2013.01)

(58) Field of Classification Search
CPC .............. A61B 17/725; A61B 17/6425; A61B 17/7013; A61F 2002/2821; A61F 2002/2825; A61F 2002/285; A61F 2002/30367; A61F 2002/30415; A61F 2002/30433; A61F 2002/30495; A61F 2002/30973
USPC ........................................ 606/62–68; 623/23
See application file for complete search history.

(56) References Cited

U.S. PATENT DOCUMENTS

| | | | | |
|---|---|---|---|---|
| 5,122,141 | A * | 6/1992 | Simpson | A61B 17/72 606/62 |
| 5,620,445 | A * | 4/1997 | Brosnahan | A61B 17/72 606/62 |
| 6,458,134 | B1 * | 10/2002 | Songer | A61B 17/68 606/304 |

(Continued)

FOREIGN PATENT DOCUMENTS

| WO | WO-96/02202 A1 | 2/1996 |
|---|---|---|
| WO | WO-96/02203 A1 | 2/1996 |

(Continued)

OTHER PUBLICATIONS

Extended European Search Report for EP App. No. 18189063.3, dated Jan. 22, 2018, 9 Pages.

*Primary Examiner* — Pedro Philogene
(74) *Attorney, Agent, or Firm* — Foley & Lardner LLP

(57) ABSTRACT

An intramedullary nail for implantation within a fractured bone. The intramedullary nail includes two or more nail modules. Each nail module has an elongated body with a first end and a second end. For each nail module, at least one of the first end or the second end is a connecting end configured to connect to a second connecting end on a second nail module.

30 Claims, 14 Drawing Sheets

(56) References Cited

U.S. PATENT DOCUMENTS

| | | | |
|---|---|---|---|
| 8,128,627 B2 * | 3/2012 | Justin | A61B 5/107 |
| | | | 606/60 |
| 8,252,002 B2 * | 8/2012 | Huff | A61F 2/4684 |
| | | | 606/102 |
| 8,764,751 B2 * | 7/2014 | Orbay | A61B 17/72 |
| | | | 606/62 |
| 10,004,916 B2 * | 6/2018 | Rogachefsky | A61N 2/008 |
| 2002/0151898 A1 | 10/2002 | Sohngen et al. | |
| 2011/0060336 A1 | 3/2011 | Pool et al. | |
| 2012/0209265 A1 | 8/2012 | Pool | |

FOREIGN PATENT DOCUMENTS

| WO | WO-2009/143374 A2 | 11/2009 |
|---|---|---|
| WO | WO-2010/135156 A1 | 11/2010 |

\* cited by examiner

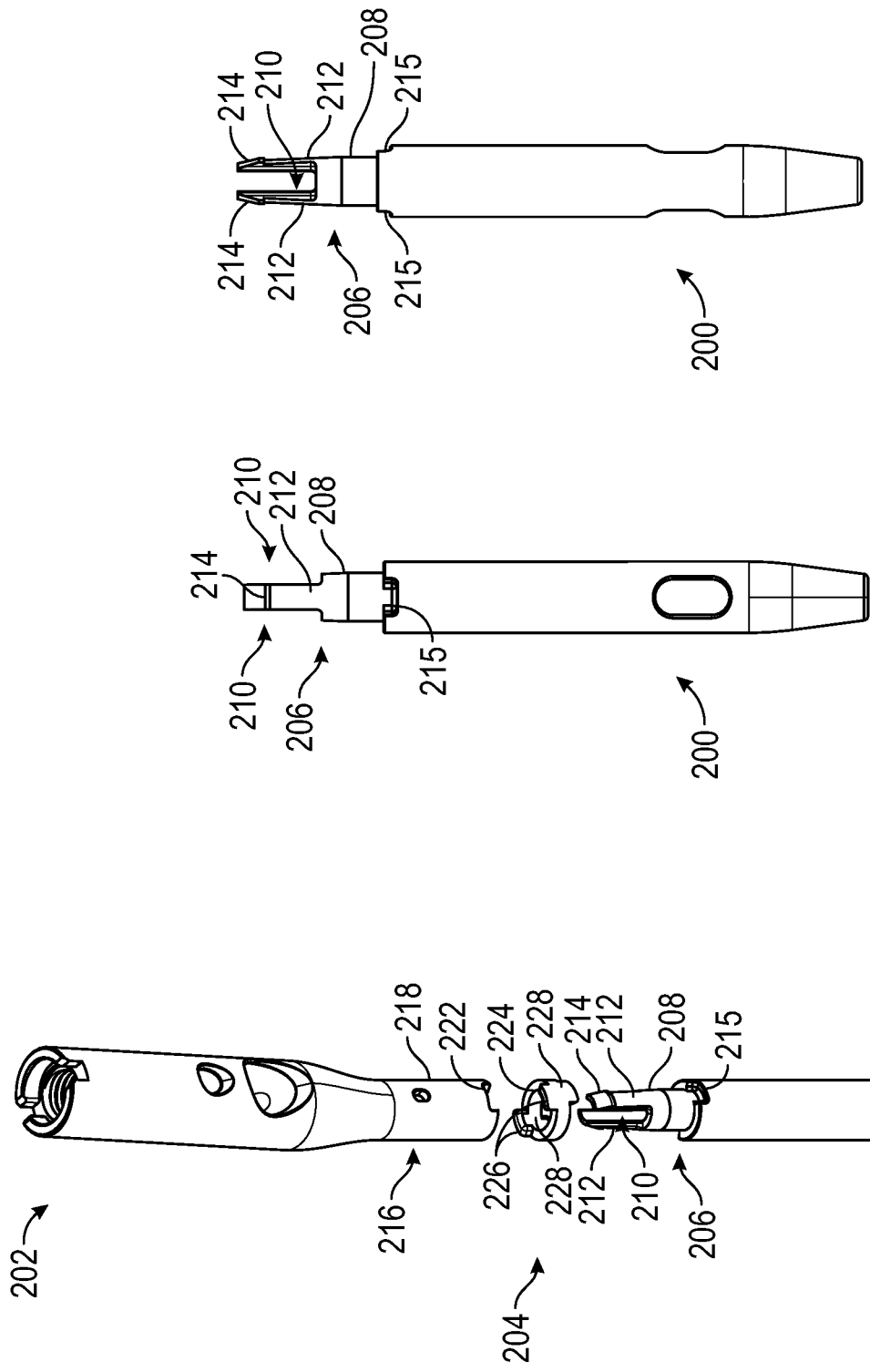

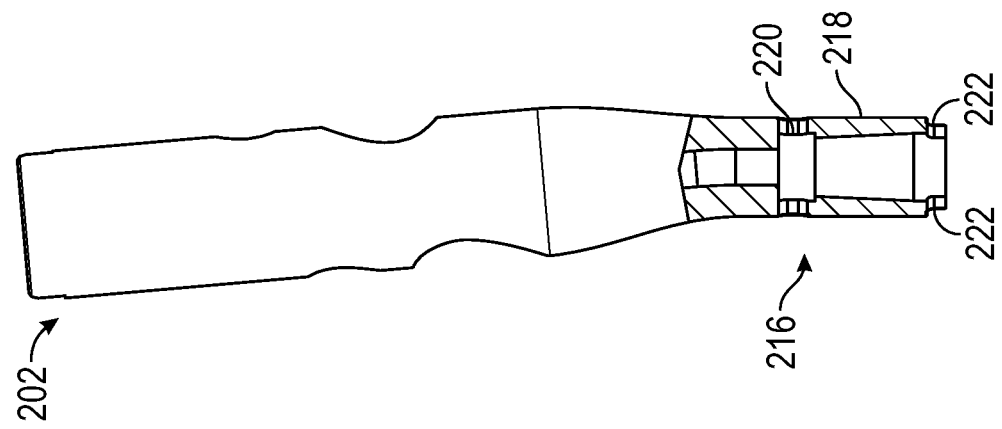
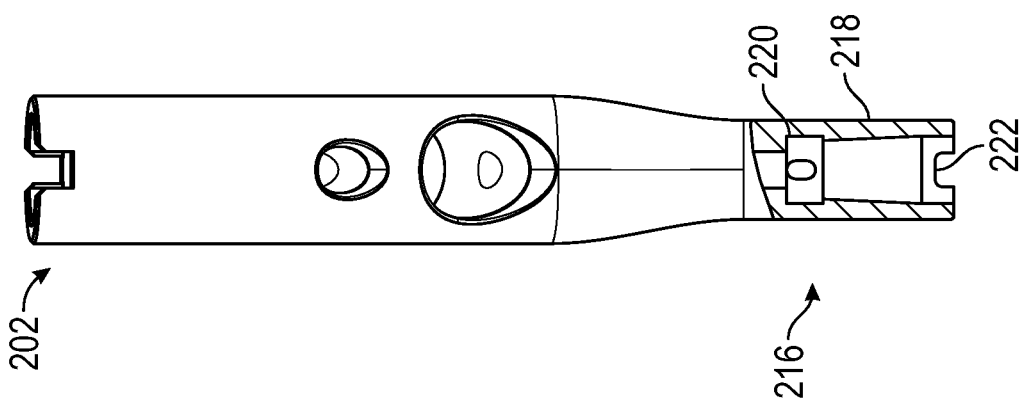
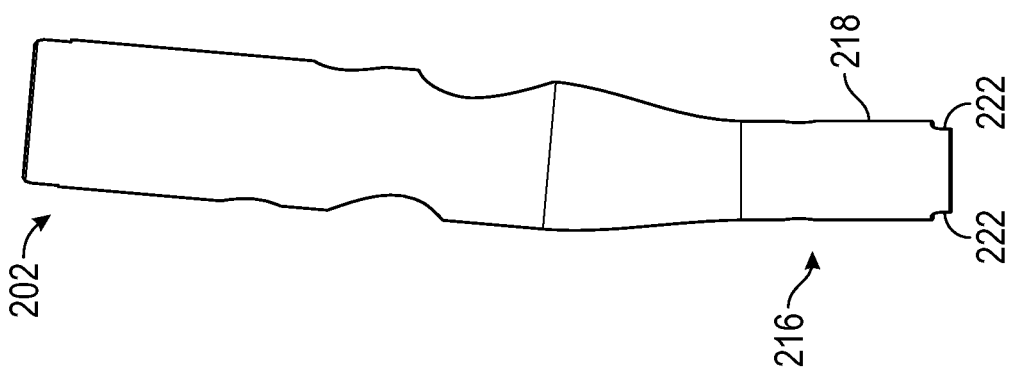
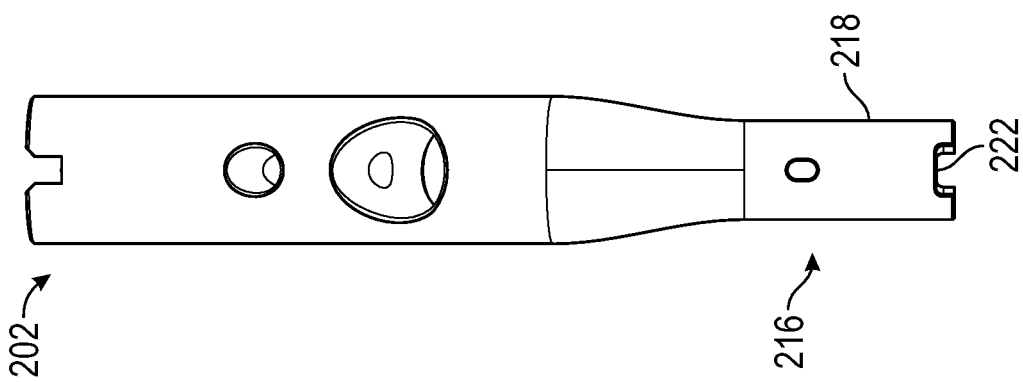

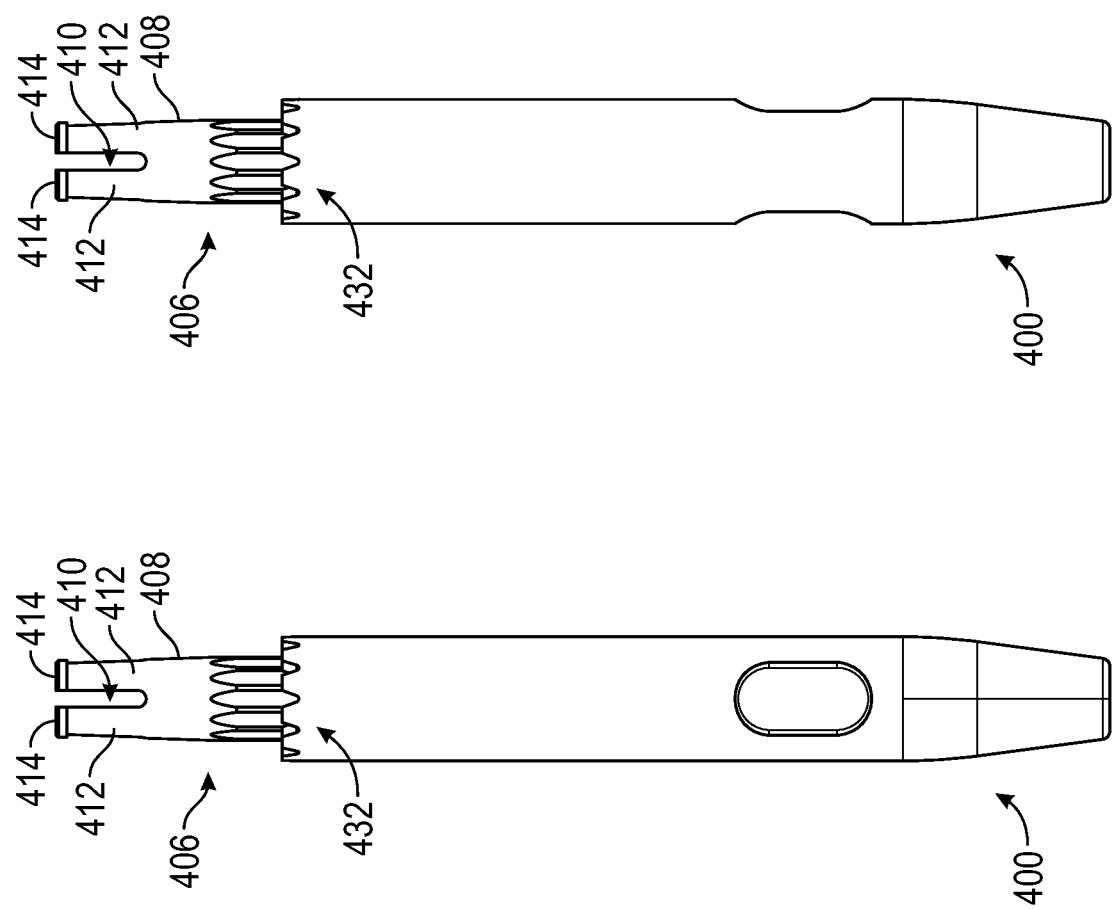

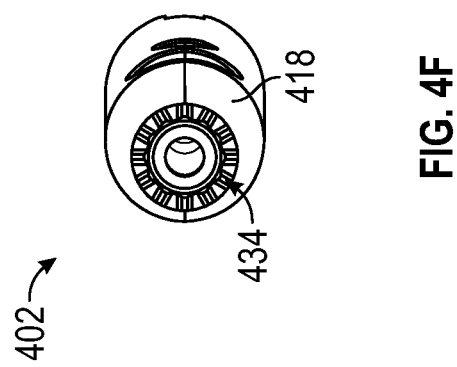
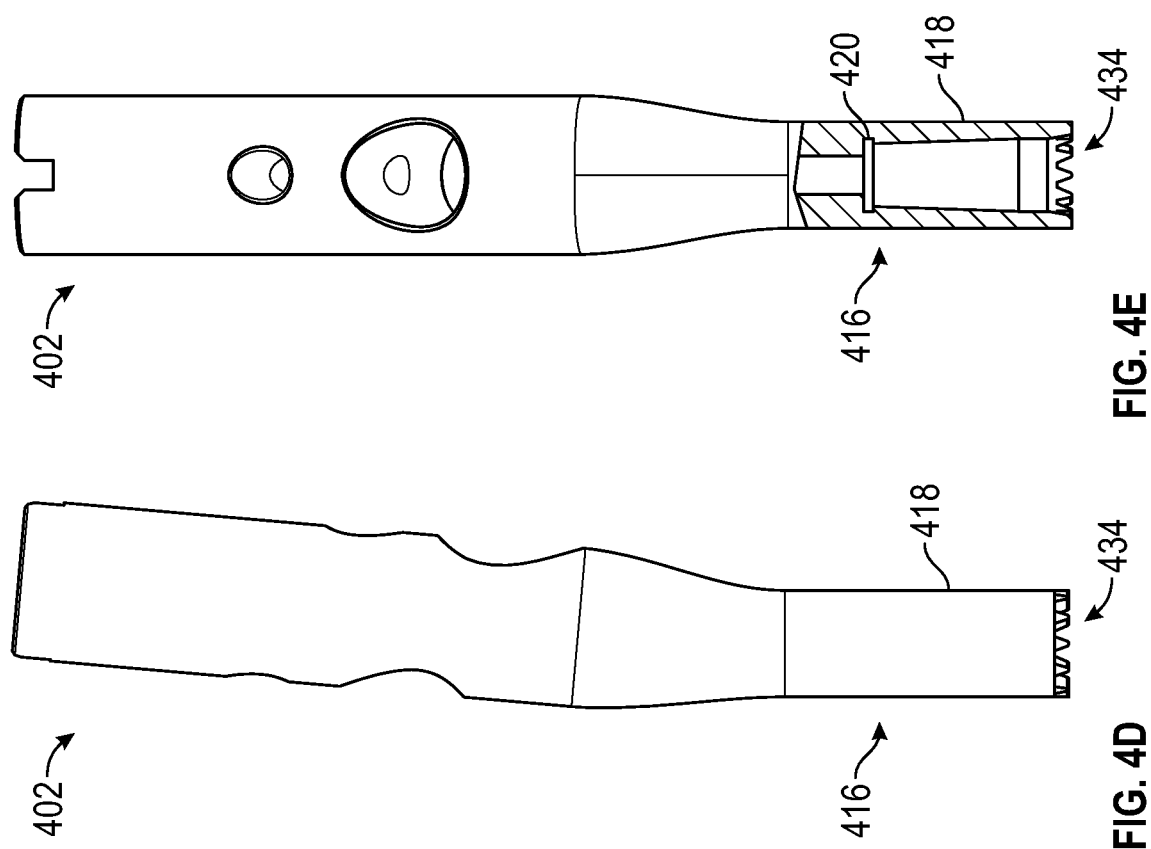

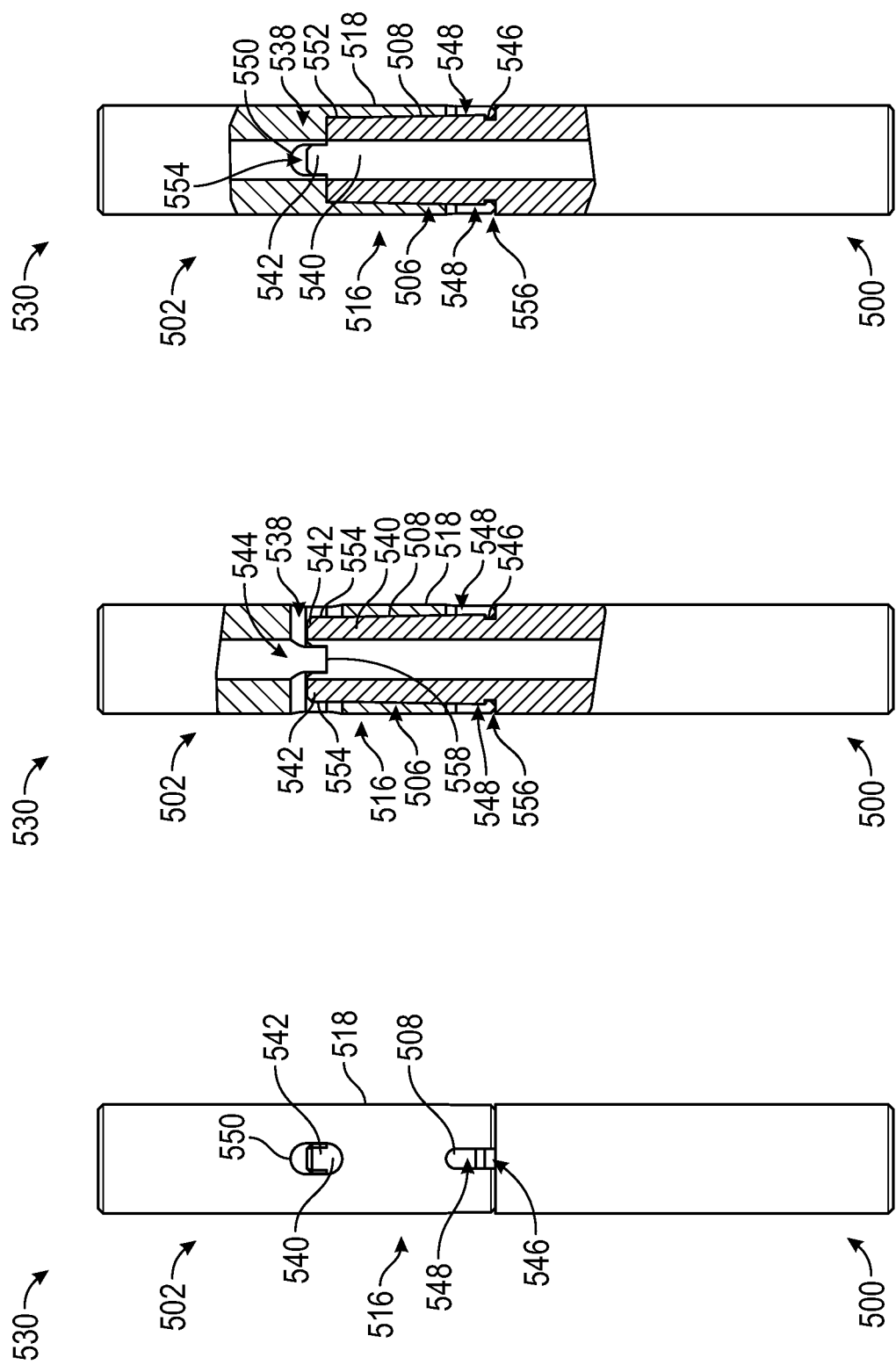

MODULAR FEMORAL NAIL AND METHOD OF USE THEREOF

BACKGROUND

In orthopedic surgeries, a nail is a fixation device designed to stabilize a fractured bone. For example, a nail may be introduced to the medullary canal of a fractured femur to stabilize the femur. Nails may be used to stabilize a variety of fractures (e.g., simple two-part fractures as well as multiple-part fractures) in a wide range of people. As such, nails are manufactured with various lengths, diameters, radii of curvature, fixation points, and so on.

SUMMARY OF THE INVENTION

One embodiment relates to an intramedullary nail for implantation within a fractured bone. The nail includes two or more nail modules. Each nail module has an elongated body with a first end and a second end. For each nail module, at least one of the first end or the second end is a connecting end configured to connect to a second connecting end on a second nail module.

Another embodiment relates to a modular intramedullary nail supply kit. The modular intramedullary nail supply kit includes a plurality of nail modules. Each nail module has an elongated body with a first end and a second end. For each nail module, at least one of the first end or the second end is a connecting end configured to connect to a second connecting end on a second nail module. A plurality of intramedullary nails can be formed by selecting and connecting at least two of the plurality of nail modules together.

Another embodiment relates to a method for building a customizable intramedullary nail. The method includes determining desired properties for the intramedullary nail and, based on the desired properties for the intramedullary nail, selecting two or more nail modules from a set of a plurality of nail modules. Each nail module has an elongated body with a first end and a second end. For each nail module, at least one of the first end or the second end is a connecting end. The method further includes connecting the two or more selected nail modules together to form the intramedullary nail by connecting at least one connecting end on each nail module with a second connecting end on a second nail module.

BRIEF DESCRIPTION OF THE DRAWINGS

FIG. 2A is a side perspective view of separated male and female nail modules and a key, according to an example embodiment.

FIGS. 2B and 2C are side views of the male nail module of FIG. 2A, according to an example embodiment.

FIGS. 2D and 2E are side views of the female nail module of FIG. 2A, according to an example embodiment.

FIGS. 2F and 2G are side views with partial cross-sections of the female nail module of FIG. 2A, according to an example embodiment.

FIGS. 4A and 4B are side views of a male nail module, according to an example embodiment.

FIG. 4C is a top view of the male nail module of FIGS. 4A and 4B, according to an example embodiment.

FIG. 4D is a side view of a female nail module, according to an example embodiment.

FIG. 4E is a side view with a partial cross-section of the female nail module of FIG. 4D, according to an example embodiment.

FIG. 4F is a bottom perspective view of the female nail module of FIG. 4D, according to an example embodiment.

FIG. 5H is a side view of the male nail module of FIGS. 5A and 5B and the female nail module of FIGS. 5D and 5E connected together, according to an example embodiment.

FIGS. 5I and 5J are side views with partial cross-sections of the male nail module of FIGS. 5A and 5B and the female nail module of FIGS. 5D and 5E connected together, according to an example embodiment.

DETAILED DESCRIPTION

Figure 1:
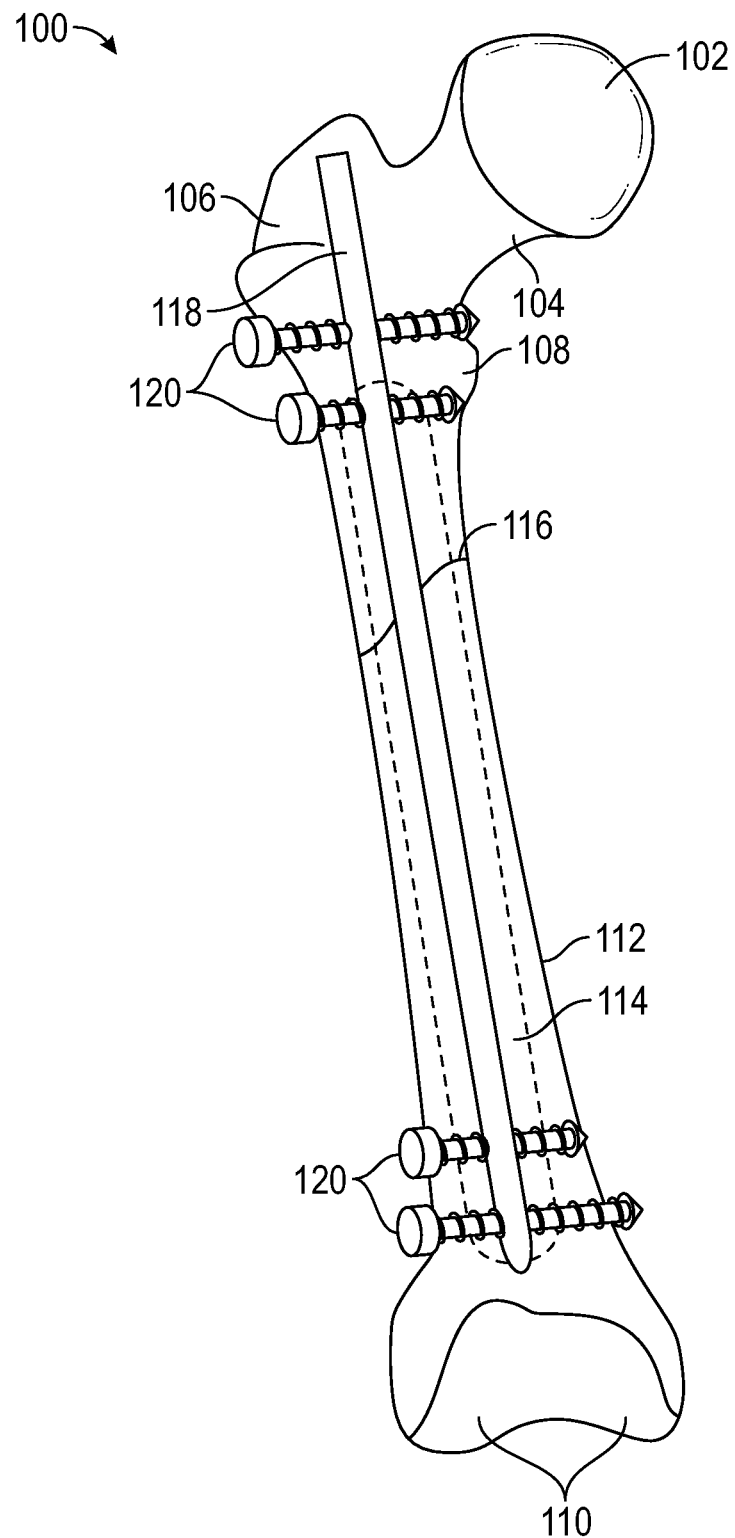
FIG. 1 is a cross-sectional view of a fractured femur with an intramedullary nail, according to an example embodiment.

When a patient suffers a fractured long bone (e.g., a bone that is longer than it is wide, such as the femur, tibia, or humerus), the fracture may be treated by inserting an intramedullary rod into the medullary cavity of the bone, the central cavity of the bone where bone marrow is stored. For example, FIG. 1 shows a femur 100 that has been fractured. The top (e.g., superior end) of the femur 100 includes a head 102 connected to a neck 104, a greater trochanter 106, and a lesser trochanter 108. The bottom (e.g., inferior end) of the femur 100 includes a pair of condyles 110. Extending between the top and the bottom of the femur 100 is a body 112 of the femur 100 containing a medullary cavity 114. As further shown in FIG. 1, the femur 100 has suffered a fracture 116. Accordingly, an intramedullary nail 118 has been inserted into the medullary cavity 114 of the femur 100 and secured in the femur 100 with screws 120. The intramedullary nail 118 aligns and stabilizes the femur 100, thereby facilitating the healing of the fracture 116. The intramedullary nail 118 may be left in the femur 100 permanently, or the intramedullary nail 118 may be removed after the fracture 116 is healed.

However, one of the difficulties of using an intramedullary nail, such as intramedullary nail 118, to stabilize a fracture is that the intramedullary nail needs to be matched to the specific anatomy of the fractured bone. For example, the same bone in different patients may have different lengths, different diameters, different bows (e.g., different levels of curvature), different bone qualities, and so on based on the patient's age, gender, and race. Additionally, the intramedullary nail should be matched to the type of fracture the patient has suffered (e.g., a simple two-part fracture versus a fracture that has broken the bone into several pieces) and which bone has suffered the fracture (e.g., a right femur versus a left femur, a tibia versus a femur). Accordingly, a surgeon who is implanting an intramedullary nail in a patient may need a variety of nails, with different angles, lengths, widths, bows, and fixation points, to select from.

Because of this, intramedullary nail manufacturers must manufacture a wide variety of intramedullary nails to meet patient needs. Further, a surgical facility must maintain an adequate supply of intramedullary nail options so that a surgeon can successfully implant an intramedullary nail into a patient to correct a fracture, particularly because unforeseen patient emergencies, unforeseen events, or inadequate surgical planning may arise. This may place significant demands on the surgical facility's acquisition and distribution department, as well as the facility's cleaning and sterilization infrastructures. Keeping an adequate stock of intramedullary nails may also be expensive, particularly with shipping costs for the variety of nails needed. Moreover, in the operating room, multiple unneeded surgical trays containing intramedullary nails may be opened to give the surgeon more treatment options, creating waste or sterilization issues. Even then, the surgeon must select from the available intramedullary nail options and has no ability to customize an intramedullary nail to fit a patient because the intramedullary nail features are static.

Accordingly, to address the manufacturing, inventory, shipping, and surgical services issues arising from the need for a variety of intramedullary nails to fit different patients, a modular intramedullary nail is provided herein. A modular intramedullary nail consists of two or more nail modules that interlock together to form an intramedullary nail. Accordingly, FIG. 2A illustrates a side perspective view of a male nail module 200 and a female nail module 202, according to an exemplary embodiment, that may be connected together to form a modular intramedullary nail. Additionally, as further shown in FIG. 2A, a modular intramedullary nail according to certain embodiments may include a key 204 configured to fit between the male nail module 200 and the female nail module 202.

Figure 2H:
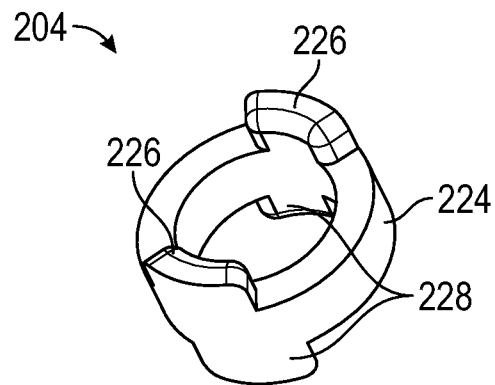
FIG. 2H is a side perspective view of the key of FIG. 2A, according to an example embodiment.

FIGS. 2B-2J show the male nail module 200, female nail module 202, and key 204 in further detail. To begin with, FIGS. 2B and 2C illustrate side views of the male nail module 200. As shown, the male nail module 200 includes a male connecting end 206, which includes an elongated section 208 set off from the rest of the male nail module 200. As shown in FIGS. 2A-2C, at least part of the elongated section 208 is hollowed out and includes two slots 210 formed into the remaining circumference of the elongated section 208 and spaced directly across from each other on the elongated section 208. The slots 210 create two prongs 212 in the remaining circumference of the elongated section 208, each of the prongs 212 narrowing and ending in a lip 214. Those of skill in the art will appreciate, however, that the elongated section of a male nail module may include more or fewer slots (e.g., such as shown on the male nail module 400 illustrated in FIGS. 4A-4C and described in further detail below), and the slots may be placed differently around the circumference of the elongated section to form different numbers and/or shapes of prongs in between the slots. Additionally, as shown in FIGS. 2A-2C, in embodiments of a modular intramedullary nail including the key 204, the bottom of the male connecting end 206 includes one or more notches 215.

FIGS. 2D and 2E illustrate side views of the female nail module 202. Similar to the male nail module 200, the female nail module 202 has a female connecting end 216. However, the female connecting end 216 instead includes a receiving section 218. As shown in FIGS. 2F and 2G, which illustrate side views of the female nail module 202 with partial cross-sections of the female connecting end 216, the receiving section 218 is hollowed out such that the receiving section 218 is configured to receive the elongated section 208 of the male nail module 200. Accordingly, the receiving section 218 further includes a groove 220 configured to receive the lips 214 of the prongs 212. Additionally, similar to the male nail module 200, in embodiments of the modular intramedullary nail including the key 204, the distal end of the female connecting end 216 includes one or more notches 222. As shown in FIGS. 2E and 2G, in some embodiments, the female nail module 202 may have a bow (e.g., the female nail module 202 may have a 3° to 5° curvature between the ends of the female nail module 202), though in other embodiments, the male nail module 200 may alternatively or additionally have a bow (e.g., the male nail module 200 may have a 3° to 5° curvature between the ends of the male nail module 200).

Figure 2I:
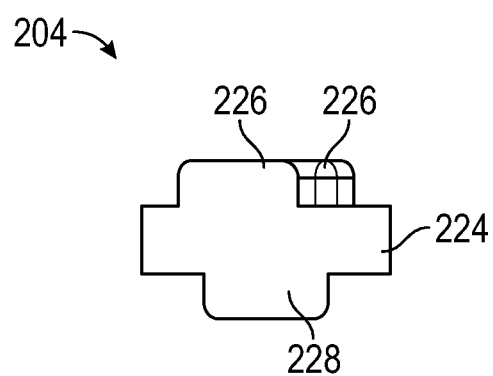
FIG. 2I is a side view of the key of FIG. 2A, according to an example embodiment.
Figure 2J:
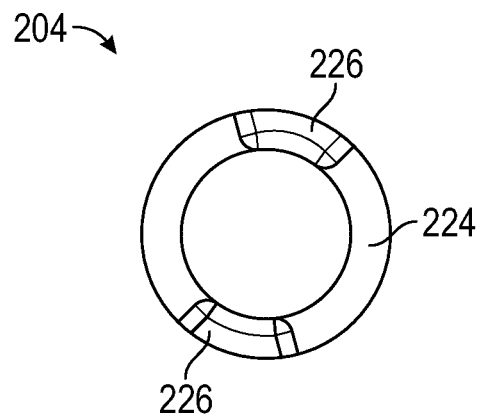
FIG. 2J is a top view of the key of FIG. 2A, according to an example embodiment.

FIG. 2H illustrates a side perspective view of the key 204, FIG. 2I illustrates a side view of the key 204, and FIG. 2J illustrates a top view of the key 204. As shown in FIGS. 2H-2J, the key 204 is formed by a ring 224 with a pair of ridges 226 projecting from the top of the ring 224 and a pair of ridges 228 projecting from the bottom of the ring 224. The top ridges 226 face each other across the ring 224, as do the bottom ridges 228. Further, as shown in FIGS. 2H and 2I, the top ridges 226 are offset from the bottom ridges 228 such that the top ridges 226 and the bottom ridges 228 do not align with each other. However, it should be appreciated that FIGS. 2H-2J show an example of a key for a modular intramedullary nail. In other embodiments, a key may include additional or fewer ridges, and the ridges may be spaced differently around the ring forming the key. Further, in other embodiments, a key may include different offsets between the top ridges and bottom ridges of the key.

Figure 2K:
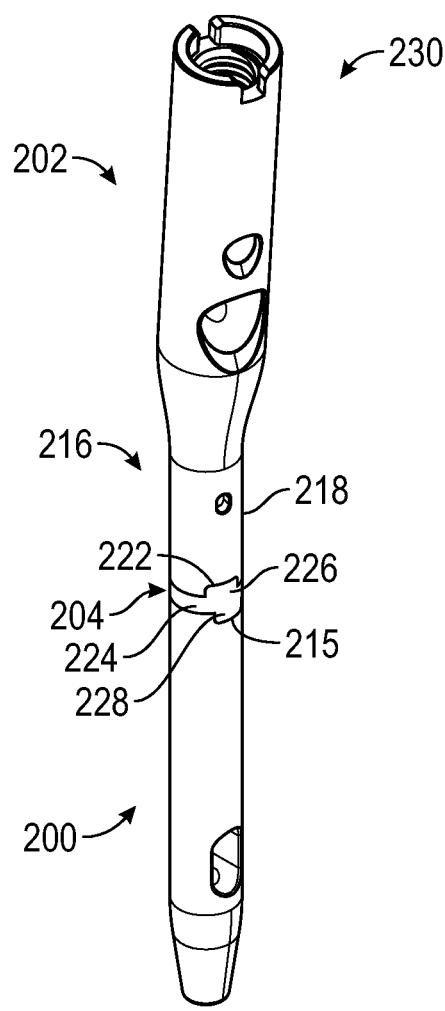
FIG. 2K is a side perspective view of the male and female nail modules and key of FIG. 2A connected together, according to an example embodiment.
Figure 2L:
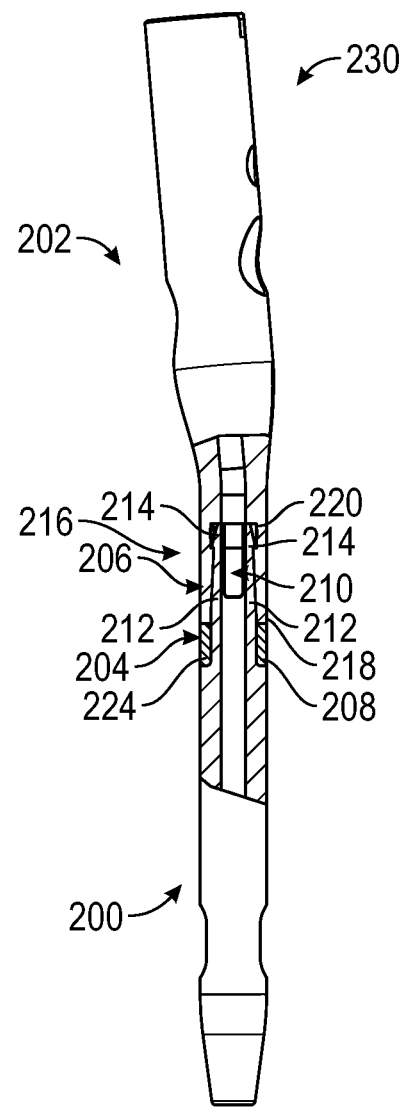
FIG. 2L is a side view with a partial cross-section of the male and female nail modules and key of FIG. 2A connected together, according to an example embodiment.

FIG. 2K shows a side perspective view of the male nail module 200, the female nail module 202, and the key 204 connected together to form a modular intramedullary nail 230. FIG. 2L shows a side view with a partial cross-section of the modular intramedullary nail 230 formed from the connected male nail module 200, female nail module 202, and key 204. As shown in FIGS. 2K and 2L, the elongated section 208 of the male connecting end 206 is configured to slide into the receiving section 218 of the female connecting end 216. The lips 214 of the prongs 212 fit inside the groove 220, thereby preventing the male connecting end 206 from slipping out of the female connecting end 216.

In embodiments including the key 204, the key 204 is configured to sit between the male connecting end 206 and the female connecting end 216, with the top ridges 226 configured to fit in the notches 222 and the bottom ridges 228 configured to fit in the notches 215. The key 204 thus prevents the male nail module 200 and the female nail module 202 from rotating relative to each other, as the notches 215 and 222 cannot slip past the ridges 226 and 228, respectively. Additionally, the key 204 is able to alter the anteversion of the modular intramedullary nail 230 (e.g., the alignment of the male nail module 200 relative to the female nail module 202). As an example, a practitioner can use a key 204 with a greater offset between the top ridges 226 and bottom ridges 228 to rotate the female nail module 202 relative to the male nail module 200 in the resulting modular intramedullary nail 230. Alternatively, a practitioner can use a key 204 with a lesser offset between the top ridges 226 and the bottom ridges 228 to provide less anteversion. Further, in certain embodiments, the key 204 may be able to alter the bow of the modular intramedullary nail 230. For example, if the ring 224 of the key 204 is wider at one end and narrower at the other end, the key 204 may be able to alter the angle of the female nail module 202 relative to the male nail module 200, thereby altering the bow of the resulting modular intramedullary nail 230 as a whole.

Figure 3:
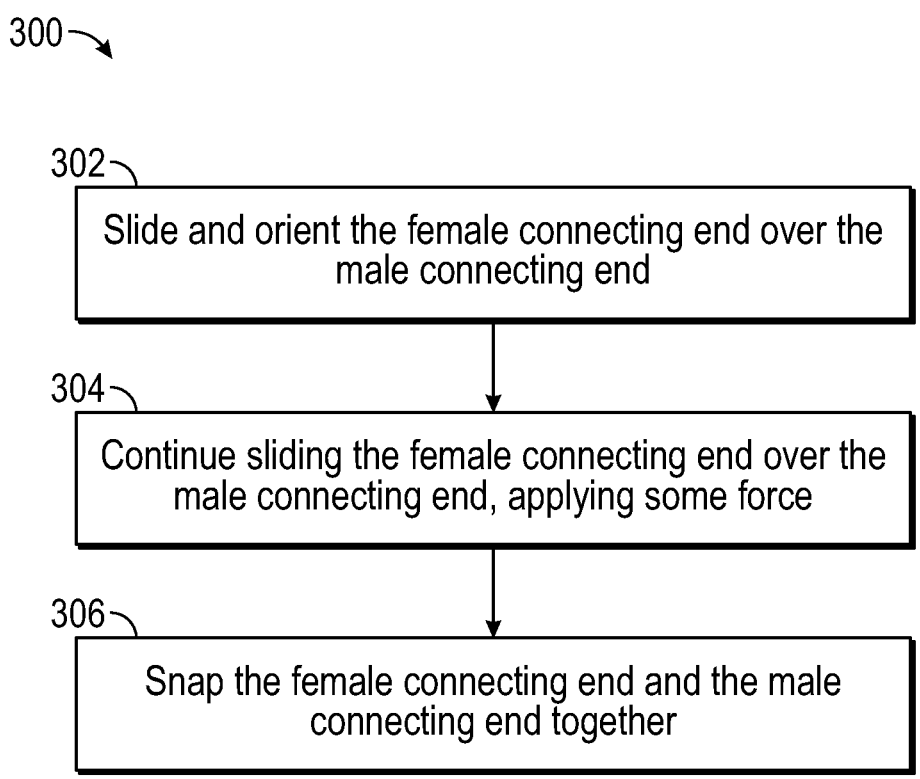
FIG. 3 is a flow diagram illustrating a method of connecting male and female nail modules, according to an example embodiment.

FIG. 3 illustrates a flow diagram showing a method 300 of connecting male and female nail modules. In describing the method 300, reference is made to the male nail module 200 and the female nail module 202. However, those of skill in the art will appreciate that the same basic method may be applied to other embodiments of male and female nail modules. First, the practitioner slides and orients the female connecting end 216 over the male connecting end 206 (302). If the a key is being used, such as the key 204, the key is slipped over the elongated section 208, such that the bottom ridges 228 fit into the notches 215. Subsequently, the receiving section 218 is inserted over the tips of the prongs 212 of the elongated section 208. Additionally, the receiving section 218 and the elongated section 208 are oriented relative to each other such that, for example, the notches 222 of the female nail module 202 align with the top ridges 226 of the key 204. At this point, only minimal force is needed to slide the female connecting end 216 over the male connecting end 206 because the prongs 212 of the elongated section 208 fit loosely within the receiving section 218.

Next, the practitioner continues sliding the female connecting end 216 over the male connecting end 206 while applying some force (304). As shown in FIGS. 2F and 2G, the hollowed out center of the receiving section 218 narrows somewhat from the distal end towards the proximal end. Accordingly, some force (e.g., reasonable hand power) must be applied to continue sliding the receiving section 218 over the elongated section 208 because, as the receiving section 218 narrows, the elongated section 208 fits more snugly within the receiving section 218, particularly due to the slightly wider lips 214 at the ends of the prongs 212. By applying some force, the prongs 212 may be deflected towards each other by the walls of the receiving section 218 (e.g., due to the slots 210), allowing the elongated section 208 to be pushed further into the receiving section 218.

Finally, the practitioner snaps the female connecting end 216 and the male connecting end 206 together (306). Accordingly, the practitioner continues applying force to push the male nail module 200 and the female nail module 202 together until the lips 214 of the prongs 212 snap into the groove 220 of the receiving section 218. In certain embodiments, the practitioner must use a connection tool to assist the practitioner in snapping the female connecting end 216 and the male connecting end 206 together (e.g., a tool to assist the practitioner in pressing the receiving section 218 over the last 6 mm of the elongated section 208). Additionally, once the female connecting end 216 and the male connecting end 206 are snapped together, the top ridges 226 of the key 204 fit into the notches 222 on the distal end of the female connecting end 216.

In some embodiments, the male nail module 200 and the female nail module 202 may be separable after they have been snapped together. For example, a practitioner may be able to pull the male nail module 200 and the female nail module 202 apart by applying a reasonable force, by using a disconnecting tool, and so on. In other embodiments, once the male nail module 200 and the female nail module 202 are snapped together, the male nail module 200 and female nail module 202 are attached together permanently.

However, those of skill in the art will appreciate that a mail nail module and a corresponding, interlocking female nail module may be designed to connect differently than depicted in FIGS. 2A-2L. For example, FIGS. 4A-4C illustrate a male nail module 400, and FIGS. 4D-4F illustrate a female nail module 402, according to a second exemplary embodiment. To begin with, FIGS. 4A and 4B illustrate a side views of the male nail module 400. Similar to the male nail module 200, the male nail module 400 includes a male connecting end 406 with an elongated section 408 set off from the rest of the male nail module 400. As shown in FIG. 4C, which illustrates a top view of the male nail module 400 (e.g., a view of the proximal end of the male nail module 400), at least part of the elongated section 408 is hollowed out, and the elongated section 408 includes four slots 410 formed into the circumference of the elongated section 408. The four slots 410 accordingly form four prongs 412 into the elongated section 408, with each prong 412 ending in a lip 414. Further, as shown in FIGS. 4A-4C, the edge of the male connecting end 406 at the bottom end (e.g., the distal end) of the elongated section 408 includes a scalloped edge 432.

FIG. 4D shows a side view of the female nail module 402, and as shown in FIG. 4D, the female nail module 402 includes a female connecting end 416. The female connecting end 416 includes a receiving section 418. FIG. 4E shows a side view of the female nail module 402 with a partial cross-section of the female connecting end 416, and FIG. 4F shows a bottom view of the female nail module 402 (e.g., a view of the distal end of the female nail module 402). As shown in FIGS. 4E and 4F, similar to the receiving section 218, the receiving section 418 is hollowed out and configured to receive the elongated section 408 of the male connecting end 406. The receiving section 418 also includes a groove 420 configured to receive the lips 414 of the prongs 412. Additionally, the distal end of the female connecting end 416 includes a scalloped edge 434 configured similarly to the scalloped edge 432 of the male nail module 400.

Figure 4H:
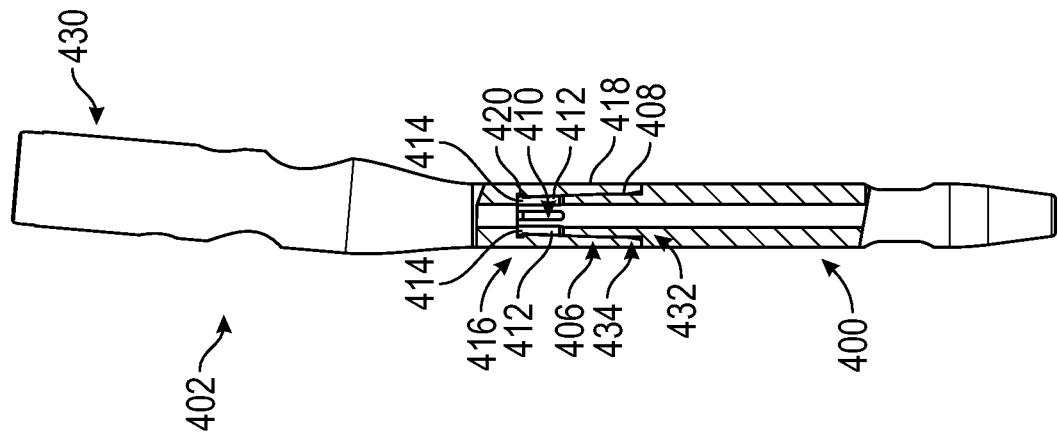
FIG. 4H is a side view with a partial cross-section of the male nail module of FIGS. 4A and 4B and the female nail module of FIG. 4D connected together, according to an example embodiment.
Figure 4G:
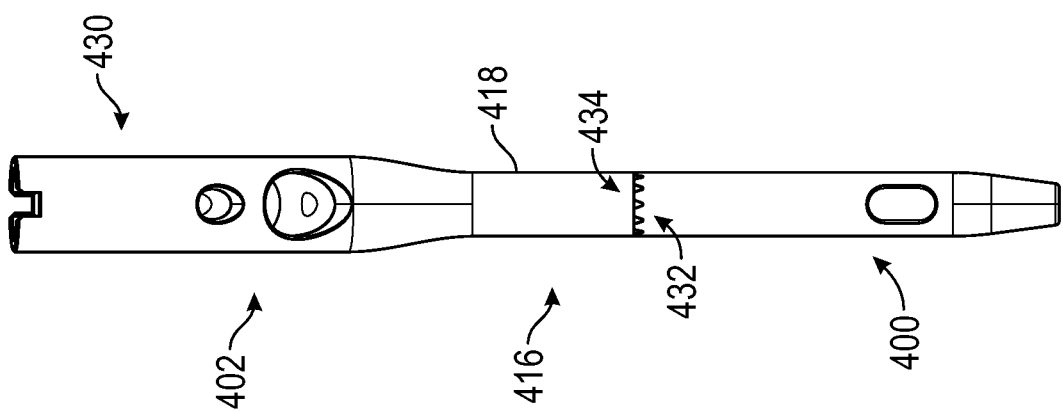
FIG. 4G is a side view of the male nail module of FIGS. 4A and 4B and the female nail module of FIG. 4D connected together, according to an example embodiment.

FIG. 4G shows a side view of the male nail module 400 and the female nail module 402 connected together to form a modular intramedullary nail 430. FIG. 4H shows a side view with a partial cross-section of the modular intramedullary nail 430 formed from the connected male nail module 400 and female nail module 402. As shown in FIG. 4H, the elongated section 408 of the male connecting end 406 is configured to slide into the receiving section 418 of the female connecting end 416. The lips 414 of the prongs 412 fit inside the groove 420 and prevent the male connecting end 406 from slipping out of the female connecting end 416. The scalloped edge 432 of the male nail module 400 is configured to fit and interlock with the scalloped edge 434 of the female nail module 402. Accordingly, scallops of the interlocked scalloped edges 432 and 434 prevent the male nail module 400 from rotating relative to the female nail module 402. Additionally, because the scalloped edges 432 and 434 each have a matching, homogenous pattern across their respective edges, the male nail module 400 and female nail module 402 may be aligned relative to each other to produce a variety of anteversions.

Figure 5A:
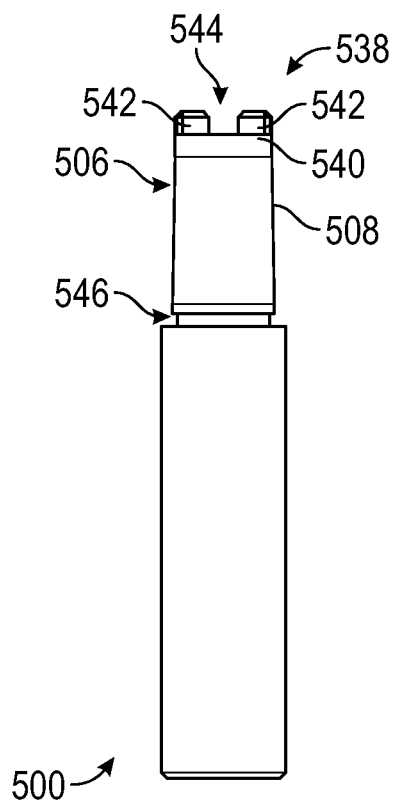
FIGS. 5A and 5B are side views of a male nail module, according to an example embodiment.
Figure 5B:
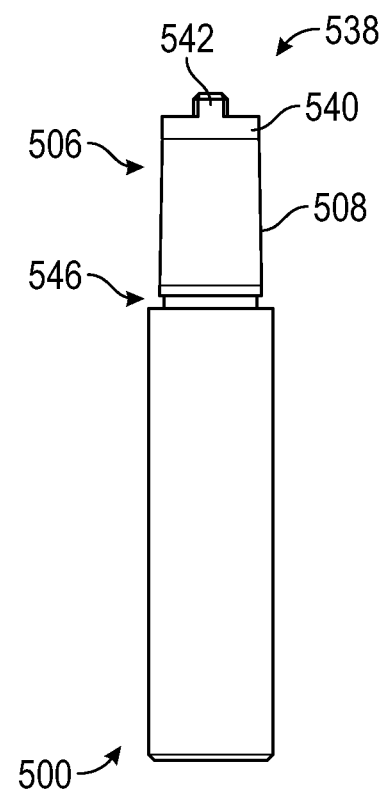
Figure 5C:
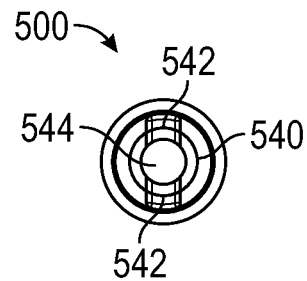
FIG. 5C is a top view of the male nail module of FIGS. 5A and 5B, according to an example embodiment.

FIGS. 5A-5C illustrate a male nail module 500, and FIGS. 5D-5G illustrate a female nail module 502, according to a third exemplary embodiment. To begin with, FIGS. 5A and 5B illustrate side views of the male nail module 500. As with the male nail modules 200 and 400, the male nail module 500 includes a male connecting end 506 with an elongated section 508 set off from the rest of the male nail module 500. The elongated section 508 tapers slightly to an end disk 540 with male anti-rotation features 542. As illustrated in FIG. 5A and in FIG. 5C, which shows a top view of the male nail module 500 (e.g., a view of the proximal end of the male nail module 500), the male anti-rotation features 542 are prongs with a separating space 544. Referring back to FIGS. 5A and 5B, the bottom of the elongated section 508 (e.g., the distal end of the elongated section 508) also includes a groove 546.

Figure 5D:
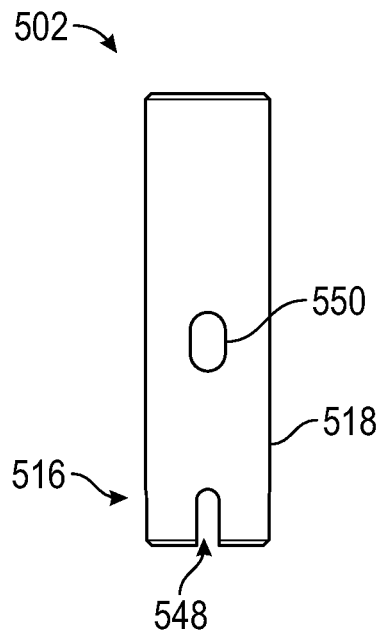
FIGS. 5D and 5E are side views of a female nail module, according to an example embodiment.
Figure 5E:
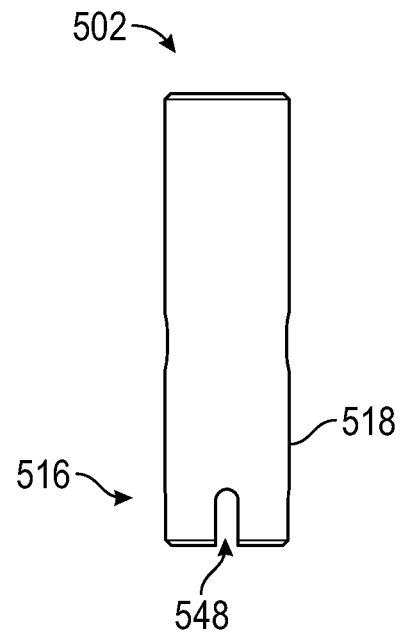
Figure 5F:
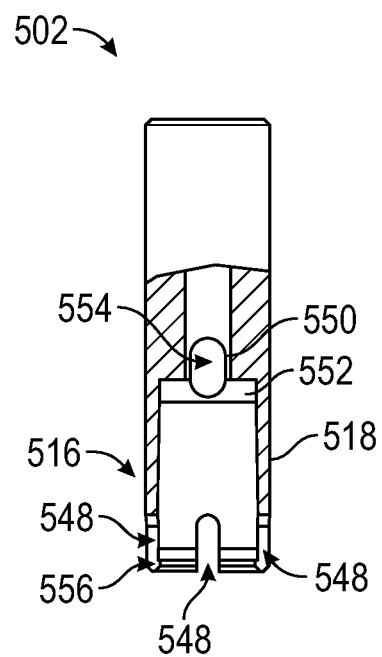
FIG. 5F is a side view with a partial cross-section of the female nail module of FIGS. 5D and 5E, according to an example embodiment.
Figure 5G:
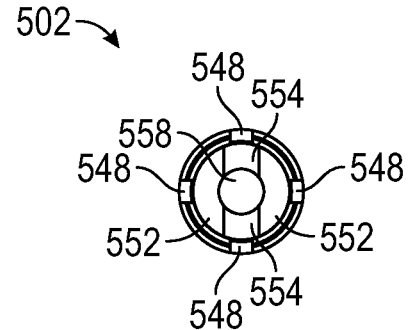
FIG. 5G is a bottom view of the female nail module of FIGS. 5D and 5E, according to an example embodiment.

FIGS. 5D and 5E show side views of the female nail module 502. Similar to the female nail modules 202 and 402, the female nail module 502 also includes a female connecting end 516 with a receiving section 518. As shown, a plurality of slots 548 are formed into the bottom (e.g., the distal end) of the receiving section 518. The slots 548 are also shown more particularly in FIG. 5F, which illustrates a side view of the female nail module 502 with a partial cross-section of the female connecting end 516. As also shown in FIG. 5F, the receiving section 518 is hollowed out and configured to receive the elongated section 508 of the male connecting end 506. The receiving section 518 can at least partially be seen through an aperture 550 formed into the wall of the female nail module 502. As illustrated in FIG. 5F, the receiving section 518 includes a disk-shaped recess 552 configured to receive the end disk 540 of the male connecting end 506. Additionally, the receiving section includes female anti-rotation features 554 configured to receive the male anti-rotation features 542. Referring to FIG. 5G, which shows a bottom view of the female nail module 502 (e.g., a view of the distal end of the female nail module 502), the female anti-rotation features 554 are separated by a protrusion 558 such that the shape of the female anti-rotation features 554 match the shape of the male anti-rotation features 542. As also shown in FIG. 5F, a lip 556 is formed into the bottom (e.g., the distal end) of the female connecting end 516.

FIG. 5H shows a side view of the male nail module 500 and the female nail module 502 connected together to form a modular intramedullary nail 530. FIGS. 5I and 5J shows side views with partial cross-sections of the modular intramedullary nail 530, formed from the connected male nail module 500 and female nail module 502. As shown in FIGS. 5I and 5J, the elongated section 508 of the male connecting end 506 is configured to slide into the receiving section 518 of the female connecting end 516. When connected, the male anti-rotation features 542 fit into the female anti-rotation features 554, thereby preventing the male nail module 500 from rotating relative to the female nail module 502. The connection of the male anti-rotation features 542 and female anti-rotation features 554 can be at least partially seen by a practitioner through the aperture 550. Additionally, the lip 556 of the female nail module 502 fits into the groove 546 of the male nail module 500 and locks the female nail module 502 and the male nail module 500 together.

Those of skill in the art will appreciate, however, that a male nail module and a female nail module may be designed with different connection mechanisms than depicted in FIGS. 2A-2L, FIGS. 4A-4H, and FIGS. 5A-5J. For example, the male nail module may instead include a peg that snaps into the female nail module, the male and female nail modules may connect through a spring lock device or a locking screw device, and so on. Moreover, the male and female nail modules may include different engagement mechanisms or features that prevent rotation and/or prevent separation of one module from an adjacent module. As an example, the male nail module may include ribbing or textures on the external surface of the male nail module that create friction once the male nail module has been inserted into the female nail module. This friction then prevents the male nail module from twisting within the female nail module. Alternatively, in some embodiments, the male and female nail modules may not include anti-rotation features. In such embodiments, the male and female nail modules may be rotated with respect to each other until a conformation that matches the fractured bone is reached. In certain embodiments, the male and female nail modules may still further be provided with a sleeve at the junction between the two modules that helps hold the modules together and/or helps prevent the modules from twisting relative to each other. Additionally, in each of the FIGS. 2A-2L, FIGS. 4A-4H, and FIGS. 5A-5J, the male nail module is shown as the distal half of the resulting intramedullary nail and the female nail module is shown as the proximal half of the resulting intramedullary nail. However, in other embodiments, the male nail module may be the proximal half and the female nail module may be the distal half.

In various embodiments, a male nail module (e.g., the male nail module 200, 400, or 500) may be connected to a female nail module (e.g., the female nail module 202 402, or 502) to create a modular intramedullary nail that is specific to the anatomy of the fractured bone. For example, a fractured bone may have a specific length, diameter, bow, orientation (e.g., right versus left), and so on. As such, a practitioner may select a male nail module and a female nail module that, when snapped together, form a modular intramedullary nail that suits or matches the length, diameter, bow, orientation, and so on of the bone to be repaired. In this respect, male and female nail modules may be manufactured in different lengths (e.g., to produce modular intramedullary nails between 180 and 500 mm in length), with different diameters (e.g., between 7 and 16 mm in diameter), with different bows (e.g., with different radii of curvature, such as between 3° to 5°), with different angles, for different bone orientations, and so on.

Further, the male nail module and the female nail module may be selected based on the type of fracture the modular intramedullary nail is repairing and the type of procedure being used to implant the modular intramedullary nail. To illustrate, with respect to a modular intramedullary nail for the femur, male and female nail modules may be selected based on whether the practitioner wishes to use a trochanter nail (e.g., with reference to FIG. 1, for insertion into the femur 100 through the greater trochanter 106), a recon nail (e.g., for fixation to the femur 100 by screwing screws through the nail and into the neck 104 and head 102 of the femur 100), an antegrade nail (e.g., for insertion into the femur 100 through the proximal end of the femur 100, such as through the greater trochanter 106), a retrograde nail (e.g., for insertion into the femur 100 through the distal end of the femur 100, such as between the condyles 110), and so on. Accordingly, the male nail module and/or the female nail module may be selected based on the configuration of the screw holes in the male nail module and/or female nail module and the locations in the bone to which the resulting modular intramedullary nail may be affixed with screws threading through the screw holes (e.g., the "fixation points" in the bone).

Figure 6A:
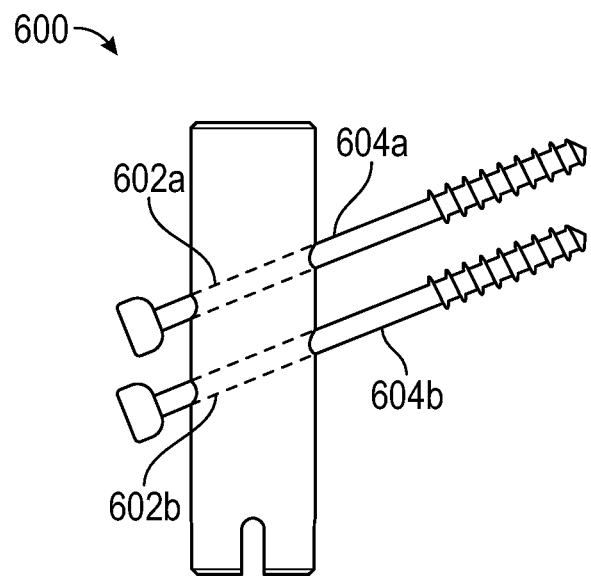
FIGS. 6A and 6B are side views of female nail module with different fixation holes, according to example embodiments.

To illustrate, FIGS. 6A-6D show examples of nail modules with various screw hole configurations that may be used in to create different types of modular intramedullary nails. In describing FIGS. 6A-6D, and the modular intramedullary nails that may be created using the nail modules shown in FIGS. 6A-6D, reference is made to the femur 100 shown in FIG. 1. To begin with, FIG. 6A shows a female nail module 600, similar to the female nail module 502, with two fixation holes 602a and 602b configured such that screws 604a and 604b threaded through the fixation holes 602a and 602b, respectively, point diagonally upwards. In one example, the module 600 is selected to create the proximal end of a recon nail, as the screws 604a and 604b can be angled through module 600 and into the neck 104 and head 102 of the femur 100 to fix the recon nail in the femur 100.

Figure 6B:
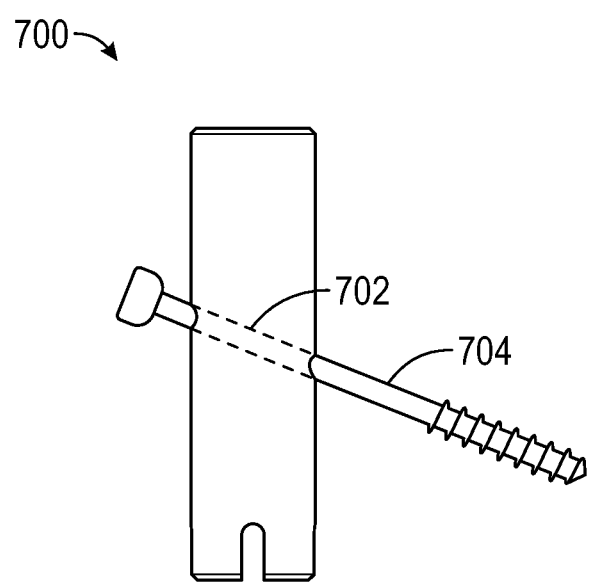

FIG. 6B shows a female nail module 700, similar to the female nail module 502, with a single fixation hole 702 configured such that a screw 704 threaded through the fixation hole 702 points diagonally downwards. As such, the module 700 may be selected to create the proximal end of a standard trochanteric nail. With the module 700 as the proximal end of a standard trochanteric nail, the screw 704 can angle downward through the module 700 and between the greater trochanter 106 and lesser trochanter 108 of the femur 100, thereby fixing the standard trochanteric nail to the femur 100.

Figure 6C:
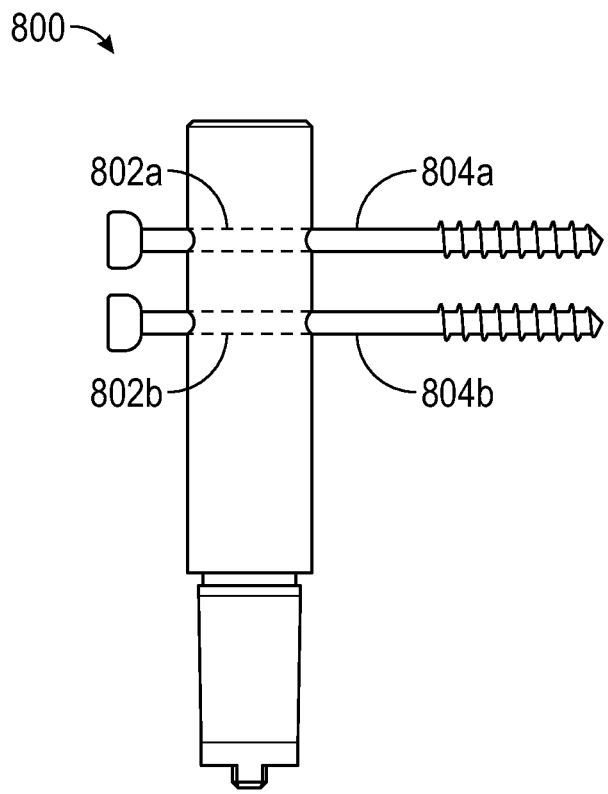
FIGS. 6C and 6D are side views of a male nail module with different fixation holes, according to example embodiments.

FIG. 6C shows a male nail module 800, similar to the male nail module 500, with fixation holes 802a and 802b. Fixation holes 802a and 802b are configured such that screws 804a and 804b threaded through the fixation holes 802a and 802b, respectively, point horizontally (e.g., perpendicular to the body of the male nail module 800). In one example, the module 800 is selected to form the distal end of a recon nail, as the screws 804a and 804b can be threaded through the module 600 and into the inferior portion of the femur 100 near the condyles 110 (e.g., similar to the intramedullary nail 118 shown in FIG. 1). In another example, the male nail module 800 may instead be a female nail module and selected to form the proximal end of a retrograde nail, with the screws 804a and 804b again fixing the retrograde nail in the inferior portion of the femur 100 near the condyles 110 or through the condyles 110.

Figure 6D:
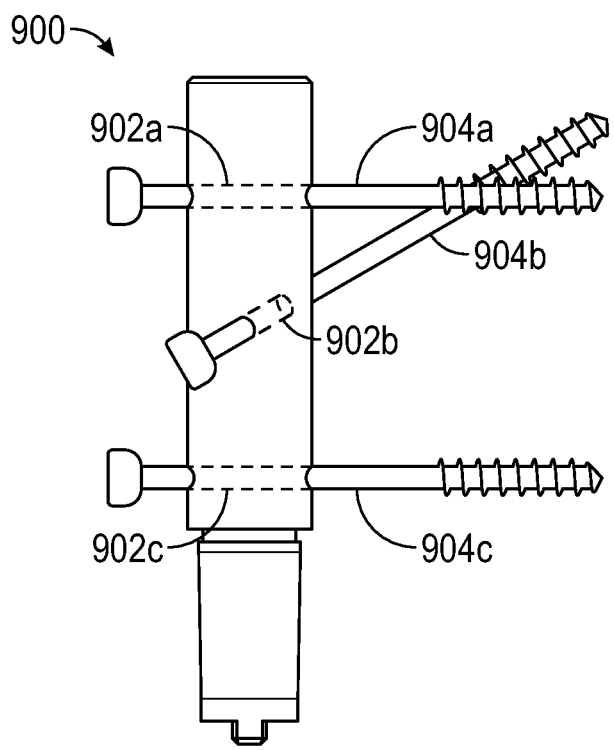

FIG. 6D shows a male nail module 900, similar to the male nail module 500, with three fixation holes 902a, 902b, and 902c configured such that screws 904a, 904b, and 904c threaded through the fixation holes 902a, 902b, and 902c, respectively, point horizontally (e.g., perpendicular to the body of the male nail module 900). However, as shown in FIG. 6D, fixation holes 902a and 902c are configured such that the screws 904a and 904c lie in a first plane, and fixation hole 902b is configured such that the screw 904b lies in a second plane. The module 900 may be selected, for example, to form the distal end of a standard trochanteric nail such that the screws 904a, 904b, and 904c anchor the distal end of the nail into the femur 100 near the condyles 110.

Those of skill in the art will appreciate, however, that modules 600, 700, 800, and 900 shown in FIGS. 6A-6D are example modules. For example, modules may be designed to have additional or fewer fixation points compared to modules 600, 700, 800, and 900 shown in FIGS. 6A-6D. Additionally, modules may be designed to have fixation points allowing for different screw angles and/or screw sizes than those shown in FIGS. 6A-6D, and modules may be designed for long bones other than the femur (e.g., the tibia or humerus) or other bones (e.g., an ankle fusion surgery). Further, while modules 600 and 700 may be designed as male nail modules, and modules 800 and 900 may be designed as female nail modules.

Modules may also be designed with various tip conformations configured to facilitate the implantation of a modular intramedullary nail. For example, as shown in FIGS. 2A and 2K, the proximal end of the female nail module 202 includes a connecting screw notch formed therein. The connecting screw notch is configured to receive a connecting screw used as part of the implantation procedure of the modular intramedullary nail 230 into the fractured bone. Once the modular intramedullary nail 230 is implanted, the connecting screw may be removed from the connecting screw notch and replaced, for example, with an end cap configured to screw into the connecting screw notch and seal off the connecting screw notch. As another example, as also shown in FIGS. 2A and 2K, the distal end of the male nail module 200 designed with a tapered tip conformation. Those of skill in the art will further appreciate, however, that modules may be manufactured with a variety of different tip conformations designed to facilitate the implantation of a modular intramedullary nail. For example, modules may be designed to serve as the distal end of a nail and include distal tip conformations such as a pointed tip, a screw tip, a threaded tip, a rounded tip, and so on. Alternatively, modules may be designed with flat tips, such as the tips shown in the male and female modules 500 and 502, as shown in FIG. 5H.

Additionally, in certain embodiments, a nail module may include further modifications or be adapted with further capabilities. As an illustration, in some embodiments, a nail module may be configured to deliver a therapeutic, such as a medication, a growth factor, and so on, to a specific portion of bone. The therapeutic may either be delivered from an internal section of the nail module or from an external section of the nail module. For example, in one embodiment, a therapeutic is stored in an internal cavity of the nail module and elutes into the bone via the screw holes of the nail module or via pores formed into the body of the nail module. In another embodiment, the nail module includes one or more external compartments or absorptive areas in which a therapeutic is stored, and the therapeutic elutes into the bone from the external compartment(s) or absorptive area(s). In yet another embodiment, the nail module includes a coating of the therapeutic on the external surface of the nail module.

Furthermore, in some embodiments, a nail module may be configured to allow the delivery of an electric current to the tissue surrounding the nail module. The nail module as a whole may serve as an electrode for the delivery of the electric current (e.g., because the nail module is made from a conductive material), or the nail module may include one or more separate electrodes formed into the body and/or ends of the nail module for the delivery of the electric current. Alternatively, or additionally, a nail module may be configured to allow the delivery of a magnetic field to the tissue surrounding the nail module. In these embodiments, the nail module may, for example, be configured to be connected to an external power source for generating the electric current and/or magnetic field. As another example, the nail module may include an internal power source (e.g., designed to fit inside a cavity of the nail module) for generating the electric current and/or magnetic field that may be rechargeable by an external power source.

In various embodiments, modular intramedullary nails may be created using more than two modules. For example, nail modules may be manufactured that include both a male connecting section and a female connecting section (e.g., both the male connecting end 206 and the female connecting end 216). These nail modules may serve as the shaft of a modular intramedullary nail, with a male nail module and a female nail module forming the proximal and distal ends of the modular intramedullary nail. Accordingly, one or more shaft nail modules may be connected to a male nail module and a female nail module, for example, to change the length or bow of an intramedullary nail. As an example, a shaft nail module with a bow of 3° to 5° may be connected between two straight male and female nail modules to create a modular intramedullary nail that matches the bow of a femur of a patient. Alternatively, several shaft nail modules may be connected between two straight male and female nail modules, with just one of the shaft nail modules having a bow or angle sufficient to change the overall bow or angle of the resulting modular intramedullary nail. As another example, shaft nail modules of various lengths may be provided to a practitioner such that the practitioner can connect shaft nail modules between a male nail module and a female nail module until the length of the resulting modular intramedullary nail matches the length of a humerus of a patient.

Further, in various embodiments, different male nail modules, female nail modules, and/or shaft nail modules may be provided in a kit such that the practitioner can create a modular intramedullary nail that is customized to the anatomy of the fractured bone, the type of fracture, and the surgery that will be used to stabilize the fracture. For example, in one embodiment, a kit may include twenty to fifty modules with different diameters (e.g., ranging between 7 and 16 mm in diameter), lengths (e.g., such that modular intramedullary nails between 180 and 500 mm in length may be created), and radii of curvature (e.g., between 3° and 5°). Additionally, the male nail modules and female nail modules may be configured with various fixation holes configured for various numbers of fixation screws and fixation angles. The practitioner can select male and female nail modules to serve as the proximal and distal ends of the modular intramedullary nail, where the male and female nail modules will create the appropriate fixation points for the intramedullary nail in the context of the fractured bone, the type of fracture being stabilized, and the surgery being used to implant the intramedullary nail. The practitioner can then build out the shaft of the modular intramedullary nail between the selected male and female nail modules by selecting shaft nail modules having the appropriate length and bow to match the anatomy of the bone being stabilized. In some embodiments, a kit of nail modules may be for a specific bone (e.g., a femur, a tibia, a humerus, or an ankle). In other embodiments, a kit of nail modules may be designed such that modular intramedullary nails configured to be implanted in a variety of bones may be created.

Those of skill in the art will appreciate that, although reference is primarily made herein to modular intramedullary nails used to treat fractured femurs, modular intramedullary nails may also be designed for a variety of other long bones. For example, modular intramedullary nails may be designed to treat fractured tibias, fibulas, humeruses, radiuses, ulnas, and so on. Modular nails may also be designed for other fixation purposes, such as to be used in an ankle fusion surgery. Additionally, modular intramedullary nails may be designed to treat a variety of fractures within a bone.

As an illustration, modular intramedullary nails for a femur may be designed to treat intertrochanteric fractures, subtrochanteric fractures, pertrochanteric fractures, femoral shaft fractures, supracondylar factures, and so on.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit, and scope of the invention. In addition, many modifications may be made to adapt a particular situation, material, composition of matter, process, process act(s) or step(s) to the objective(s), spirit or scope of the present invention. Further, as will be appreciated by those with skill in the art, each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

The invention includes methods that may be performed using the subject devices. The methods may include the act of providing such a suitable device. Such provision may be performed by the end user. In other words, the "providing" act merely requires the end user obtain, access, approach, position, set-up, activate, power-up, or otherwise act to provide the requisite device in the subject method. Methods recited herein may be carried out in any order of the recited events that is logically possible, as well as in the recited order of events.

Exemplary aspects of the invention have been set forth above. As for other details of the present invention, these may be appreciated in connection with patents and publications generally known or appreciated by those with skill in the art. The same may hold true with respect to method-based aspects of the invention in terms of additional acts as commonly or logically employed by those with skill in the art.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "'solely,"

"only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims or the addition of a feature could be regarded as transforming the nature of an element set forth in such claims. Except as specifically defined herein, all technical and scientific terms used herein are to be given as broad a commonly understood meaning as possible while maintaining claim validity.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

The breadth of the present invention is not to be limited to the examples provided and/or the subject specification, but rather only by the scope of claim language associated with this disclosure.

What is claimed is:

1. An intramedullary nail for implantation within a fractured bone, the nail comprising:
    two or more nail modules, each nail having an elongated body with a first end and a second end;
    wherein at least one of the first end or the second end of a first nail module is a connecting end configured to connect to a second connecting end on a second nail module; and
    an engagement mechanism configured to rigidly couple the first nail module to the second nail module to prevent relative movement between the first nail module and the second nail module the engagement mechanism comprising:
        an elongated portion protruding axially from the connecting end of the first nail module, wherein the elongated portion further comprises a hollowed-out section having two or more prongs in an outer circumference of the hollowed-out section; and
        a recess extending axially into the connecting end of the second nail module, the recess configured to receive the two or more prongs.

2. The intramedullary nail of claim 1, wherein each connecting end is one of a male connecting end or a female connecting end and is configured to connect to the other of the male connecting end or the female connecting end on a second nail module.

3. The intramedullary nail of claim 1, wherein each connecting end comprises at least one notch, and wherein the intramedullary nail further comprises a key comprising a ring with a top side and a bottom side and at least one ridge formed on each side, the key configured to interlock between the connecting ends of two nail modules with the ridges of the key fitting in the notches of the connecting ends.

4. The intramedullary nail of claim 3, wherein the at least one top ridge is offset from the at least one bottom ridge.

5. The intramedullary nail of claim 1, wherein each connecting end includes a scalloped edge such that scallops on one scalloped edge are configured to interlock with scallops on another scalloped edge.

6. The intramedullary nail of claim 1, wherein at least one of each connecting end or each second connecting end includes an anti-rotation feature configured to prevent the nail module from rotating relative to the second nail module.

7. The intramedullary nail of claim 1, wherein the two or more nail modules are selected and connected together in a configuration that provides the intramedullary nail with at least one of a length, a diameter, a bow, an orientation, or fixation points suited to at least one of an anatomy of the fractured bone, a type of fracture in the fractured bone, or a type of procedure used to implant the intramedullary nail in the fractured bone.

8. The intramedullary nail of claim 1, wherein the intramedullary nail has a proximal end and a distal end, and wherein at least one of a nail module forming the proximal end or the nail module forming the distal end has a tip conformation configured to facilitate implantation of the intramedullary nail in the fractured bone.

9. The intramedullary nail of claim 1, wherein the intramedullary nail has a shaft extending between a proximal end and a distal end, the intramedullary nail further comprising:
    a proximal end nail module configured to form the proximal end of the intramedullary nail, wherein one of the first end or the second end of the proximal end nail module is a connecting end;
    a distal end nail module configured to form the distal end of the intramedullary nail, wherein one of the first end or the second end of the distal end nail module is a connecting end; and
    one or more shaft nail modules configured to form the shaft of the intramedullary nail, wherein the first end and the second end of each shaft nail module is a connecting end.

10. The intramedullary nail of claim 1, wherein at least one of the two or more nail modules is configured to release a therapeutic.

11. The intramedullary nail of claim 1, wherein at least one of the two or more nail modules is configured to deliver at least one of an electric current or a magnetic field.

12. A modular intramedullary nail supply kit comprising:
    a plurality of nail modules, each nail module having an elongated body with a first end and a second end;
    wherein at least one of the first end or the second end of a first nail module is a connecting end configured to connect to a second connecting end on a second nail module; and
    wherein a plurality of intramedullary nails can be formed by selecting and connecting at least two of the plurality of nail modules together;
    wherein at least one of the plurality of nail modules comprises an engagement mechanism configured to rigidly couple the first nail module to the second nail module to prevent relative movement between the first nail module and the second nail module, the engagement mechanism comprising:
        an elongated portion protruding axially from the connecting end of the first nail module, wherein the elongated portion further comprises a hollowed-out section having two or more prongs in an outer circumference of the hollowed-out section; and
        a recess extending axially into the connecting end of the second nail module, the recess configured to receive the two or more prongs.

13. The modular intramedullary nail supply kit of claim 12, wherein each connecting end is one of a male connecting end or a female connecting end and is configured to connect to the other of the male connecting end or the female connecting end on a second nail module.

14. The modular intramedullary nail supply kit of claim 12, wherein each connecting end comprises at least one notch, and wherein the kit further comprises a plurality of keys, each key comprising a ring with a top side and a bottom side and at least one ridge formed on each side, the key configured to interlock between the connecting ends of two nail modules with the ridges of the key fitting in the notches of the connecting ends.

15. The modular intramedullary nail supply kit of claim 14, wherein, for at least some of the keys, the at least one top ridge is offset from the at least one bottom ridge.

16. The modular intramedullary nail supply kit of claim 12, wherein each connecting end includes a scalloped edge such that scallops on one scalloped edge are configured to interlock with scallops on another scalloped edge.

17. The modular intramedullary nail supply kit of claim 12, wherein at least one of each connecting end or each second connecting end includes an anti-rotation feature configured to prevent the nail module from rotating relative to the second nail module.

18. The modular intramedullary nail supply kit of claim 12, wherein properties of the plurality of nail modules comprise at least one of a plurality of nail module lengths, a plurality of nail module diameters, or a plurality of nail module radii of curvature.

19. The modular intramedullary nail supply kit of claim 12, wherein the plurality of nail modules comprises two or more nail modules having one or more fixation holes formed in a body of each of the one or more nail modules, each fixation hole configured to receive a fixation screw and the two or more nail modules having at least two different fixation hole configurations.

20. The modular intramedullary nail supply kit of claim 12, wherein the plurality of nail modules comprises one or more nail modules including a tip conformation at the first end or the second end of each of the one or more nail modules, each tip conformation configured to facilitate implantation of an intramedullary nail including a nail module with the tip conformation in a fractured bone.

21. The modular intramedullary nail supply kit of claim 12, wherein some of the plurality of nail modules are proximal end nail modules configured to form a proximal end of an intramedullary nail, each proximal end nail module having a connecting end on either the first end or the second end;
wherein some of the plurality of nail modules are distal end nail modules configured to form a distal end of an intramedullary nail, each distal end nail module having a connecting end on either the first end or the second end; and
wherein some of the plurality of nail modules are shaft nail modules configured to form a shaft of an intramedullary nail, each shaft nail module having a connecting end on both the first end and the second end.

22. A method for building a customizable intramedullary nail, the method comprising:
determining desired properties for the intramedullary nail;
based on the desired properties for the intramedullary nail, selecting two or more nail modules from a set of a plurality of nail modules, each nail module having an elongated body with a first end and a second end, wherein, for each nail module, at least one of the first end or the second end is a connecting end; and
rigidly connecting the two or more selected nail modules together to form the intramedullary nail by connecting at least one connecting end on each nail module with a second connecting end on a second nail module;
wherein rigidly connecting the two or more selected nail modules together uses an engagement mechanism configured to rigidly couple the first nail module to the second nail module to prevent relative movement between the first nail module and the second nail module, the engagement mechanism comprising:
an elongated portion protruding axially from the connecting end of the first nail module, wherein the elongated portion further comprises a hollowed-out section having two or more prongs in an outer circumference of the hollowed-out section; and
a recess extending axially into the connecting end of the second nail module, the recess configured to receive the two or more prongs.

23. The method of claim 22, wherein each connecting end is one of a male connecting end or a female connecting end and is configured to connect to the other of the male connecting end or the female connecting end on a second nail module.

24. The method of claim 22, wherein each connecting end comprises at least one notch, and wherein the method further comprises:
selecting at least one key from a plurality of keys, each key comprising a ring with a top side and a bottom side and at least one ridge formed on each side and each key configured to interlock between the connecting ends of two nail modules with ridges of the key fitting in the notches of the connecting ends; and
wherein connecting the two or more selected nail modules comprises connecting the two or more selected nail modules such that each selected key is positioned between a pair of the connected nail modules.

25. The method of claim 22, wherein, for at least one selected key, the at least one top ridge is offset from the at least one bottom ridge.

26. The method of claim 22, wherein each connecting end includes a scalloped edge such that scallops on one scalloped edge are configured to interlock with scallops on another scalloped edge.

27. The method of claim 22, wherein at least one of each connecting end or each second connecting end includes an anti-rotation feature configured to prevent the nail module from rotating relative to the second nail module.

28. The method of claim 22, wherein the desired properties for the intramedullary nail comprise at least one of a length, a diameter, a bow, an orientation, or fixation points, and wherein determining the desired properties for the intramedullary nail is based on at least one of an anatomy of a fractured bone in which the intramedullary nail will be implanted, a type of fracture in the fractured bone, or a type of procedure used to implant the intramedullary nail in the fractured bone.

29. The method of claim 22, wherein the intramedullary nail has a proximal end and a distal end, and wherein selecting the two or more nail modules comprises at least one of:
selecting, to form the proximal end, a nail module with a tip conformation configured to facilitate implantation of the intramedullary nail in a fractured bone; or
selecting, to form the distal end, a nail module with a tip conformation configured to facilitate implantation of the intramedullary nail in the fractured bone.

30. The method of claim 22, wherein the intramedullary nail has a proximal end and a distal end;

wherein selecting the two or more nail modules comprises:

selecting a proximal end nail module configured to form the proximal end of the intramedullary nail, wherein one of the first end or the second end of the proximal end nail module is a connecting end;

selecting a distal end nail module configured to form the distal end of the intramedullary nail, wherein one of the first end or the second end of the distal end nail module is a connecting end; and selecting one or more shaft nail modules, wherein the first end and the second end of each shaft module is a connecting end; and wherein connecting the two or more selected nail modules together comprises connecting the one or more shaft nail modules between the proximal end nail module and the distal end nail module.

* * * * *